(12) United States Patent
Shanler et al.

(10) Patent No.: US 8,114,898 B2
(45) Date of Patent: Feb. 14, 2012

(54) COMPOSITIONS AND METHODS FOR TREATING PURPURA

(75) Inventors: Stuart D. Shanler, Pamona, NY (US); Andrew Ondo, Las Cruces, NM (US)

(73) Assignee: Allergan, Inc., Irvine, CA (US)

( * ) Notice: Subject to any disclaimer, the term of this patent is extended or adjusted under 35 U.S.C. 154(b) by 330 days.

(21) Appl. No.: 12/272,253

(22) Filed: Nov. 17, 2008

(65) Prior Publication Data

US 2009/0130027 A1 May 21, 2009

Related U.S. Application Data

(60) Provisional application No. 60/988,564, filed on Nov. 16, 2007.

(51) Int. Cl.
| | |
|---|---|
| *A61K 31/133* | (2006.01) |
| *A61K 31/4172* | (2006.01) |
| *A61K 31/4164* | (2006.01) |
| *A61K 31/382* | (2006.01) |
| *A61K 31/4174* | (2006.01) |
| *A61K 31/03* | (2006.01) |
| *A61K 31/155* | (2006.01) |
| *A61K 31/05* | (2006.01) |
| *A01N 43/50* | (2006.01) |
| *A01N 43/54* | (2006.01) |
| *A01N 33/02* | (2006.01) |

(52) U.S. Cl. ........ 514/393; 514/385; 514/646; 514/622; 514/601; 514/252.1; 514/595; 514/227.2

(58) Field of Classification Search .................. None
See application file for complete search history.

(56) References Cited

U.S. PATENT DOCUMENTS

| | | | |
|---|---|---|---|
| 4,853,216 | A | 8/1989 | Koslo et al. |
| 6,335,023 | B1 | 1/2002 | Yu et al. |
| 6,824,786 | B2 | 11/2004 | Yu et al. |
| 2002/0103162 | A1 * | 8/2002 | Epstein et al. .......... 514/79 |
| 2003/0108496 | A1 | 6/2003 | Yu et al. |
| 2004/0220259 | A1 | 11/2004 | Yu et al. |
| 2004/0242588 | A1 | 12/2004 | Dejovin et al. |
| 2005/0020600 | A1 | 1/2005 | Scherer |
| 2005/0165079 | A1 | 7/2005 | Shanler et al. |
| 2005/0222101 | A1 | 10/2005 | Hutterer |
| 2005/0256204 | A1 | 11/2005 | Bitter, Sr. |
| 2005/0271596 | A1 | 12/2005 | Friedman et al. |
| 2005/0276830 | A1 | 12/2005 | DeJovin et al. |
| 2005/0281772 | A1 | 12/2005 | Bromley et al. |
| 2006/0171974 | A1 | 8/2006 | DeJovin et al. |
| 2006/0264515 | A1 | 11/2006 | Dejovin et al. |
| 2007/0048234 | A1 | 3/2007 | Waugh et al. |
| 2007/0082070 | A1 | 4/2007 | Stookey et al. |
| 2007/0225217 | A1 | 9/2007 | Chappell et al. |
| 2007/0225631 | A1 | 9/2007 | Bowlin et al. |

FOREIGN PATENT DOCUMENTS

| | | |
|---|---|---|
| WO | WO 2004/060172 A1 | 7/2004 |
| WO | WO 2009/082452 A1 | 7/2009 |

OTHER PUBLICATIONS

Cohen, Chapter 65: Rash-petechiae and purpura, in Textbook of Pediatric emergency Medicine 5th Edition. Fleisher et al. Eds., Lippinocott Williams &Wilkins: Philiadelphia, 2006.*
Shepro et al. (Thromb. Res. 1984, 35, 421-30).*
George et al. (Ann. Intern. Med. 1998:129:886-890).*
Blajchman et al. J. Clin. Invest. 1979, 63, 1026-1035.*
Bamford et al. "Rosacea: Current Thoughts on Origin" 2001, Seminars in Cutaneous Medicine and Surgery, 20(3):199-206.
Crawford et al. "Rosacea: I. Etiology, Pathogenesis, and Subtype Classification" 2004, J. Am. Acad. Dermatol., 51(3)324-41.
Cunliffe et al. "Clonidine and Facial Flushing in Rosacea" 1977, British Med. J., 105.
Sams "Untoward Response with Topical Fluoruracil" 1968, Arch. Dermatol. 97(1): 14-22.
Collagenex Corporation/IMS Demand Study as presented at The Fourth Annual Healthcare Conference, Nov. 27-28, 2007, New York, NY.
van Zuuren et al. "Systematic Review of Rosacea Treatments" 2007, J. Am. Acad. Dermatol. 56:107-115.
Powell "Clinical Practice: Rosacea" 2005, N. Engl. J. Med. 352(8):793-803.
Fisher "Adverse Effects of Topical Corticosteroid Use" 1995, West. J. Med. 162:123-126.
Crawford et al., Rosacea: I. Etiology, Pathogenesis, and Subtype Classification, Sep. 2004, J. Am. Acad. Dermatol. 51(3):327-341.
Pelle et al., Rosacea: II. Therapy, Oct. 2004, J. Am. Acad. Dermatol. 51(4):499-512.
Wilkin et al., Standard Classification of Rosacea: Report of the National Rosacea Society Expert Committee on the Classification and Staging of Rosacea, 2002, J. Am. Acad. Dermatol. 46(4):584-587.
Plewig et al., Acne and Rosacea, $2^{nd}$ Rev. Ed., Springer-Verlag, Berlin, pp. 433-475.
Wilkin, Why is Flushing Limited to a Mostly Facial Cutaneous Distribution?, Aug. 1988, J. Am. Acad. Dermatol. 2(1):309-313.

(Continued)

*Primary Examiner* — Johann Richter
*Assistant Examiner* — Jessica Kassa
(74) *Attorney, Agent, or Firm* — Pepper Hamilton LLP

(57) ABSTRACT

Embodiments of the present invention are directed to compositions and methods for the treatment of purpura. Preferred compositions comprise an α adrenergic receptor agonist selected from selective $\alpha_1$ adrenergic receptor agonist, selective $\alpha_2$ adrenergic receptor agonist, non-selective $\alpha_1/\alpha_2$ adrenergic receptor agonist, agents with $\alpha_2$ adrenergic receptor agonist activity and combinations thereof, in a pharmaceutically acceptable carrier in order to treat and improve the cosmetic appearance of hemorrhagic (purpuric) lesions in the skin.

33 Claims, No Drawings

OTHER PUBLICATIONS

Wilkin, Oral Thermal-Induced Flushing in Erythematotelangiectatic Rosacea, 1981, J. Invest. Dermatol. 76(1):15-18.
Parodi et al., Flushing in Rosacea: An Experimental Approach, 1980, Archives of Dermatol. Res., Springer-Verlag, 269:269-273.
Ahlquist, A Study of the Adrenotropic Receptors, Jun. 1948, Adrenotropic Receptors 153:586-600.
Kirstein et al., Autonomic Nervous System Pharmacogenomics: A Progress Report, 2004, Pharmacol. Rev. 56(1):31-52.
Piascik et al., $\alpha_1$-Adrenergic Receptors: New Insights and Directions, 2001, J. Pharmacol. and Exper. Therap. 298(2):403-410.
Calzada et al., Alpha-Adrenoceptor Subtypes, 2001, Pharmacol. Res. 44(3):195-207.
Guimaraes et al., Vascular Adrenoceptors: An Update, 2001, Am. Soc. Pharmacol. and Exper. Therapeutics, Pharmacol. Rev. 53(2):319-356.
Hieble, Subclassification and Nomenclature of $\alpha$-and $\beta$-Adrenoceptors, 2007, Curr. Topics in Medicinal Chem. 7:129-134.
Jarajapu et al., Functional Characterization of $\alpha_1$-Adrenoceptor Subtypes in Human Subcutaneous Resistance Arteries, 2001, J. Pharmacol. and Exp. Therapeutics 299(2):729-734.
Leech et al., Different $\alpha$-adrenoceptor Subtypes Mediate Constriction of Arterioles and Venules, 1996, Am. Phys. Soc., pp. H710-H722.
Chalothorn et al., Differences in the Cellular Localization and Agonist-Mediated Internalization Properties of the $\alpha_1$-Adrenoceptor Subtypes, 2002, Molec. Pharmacol. 61(5):1008-1016.
Bishop, Recent Advances in the Discovery of $\alpha_1$-Adrenoceptor Agonists, 2007, Curr. Topics Med. Chem. 7:135-145.
Crassous et al., Interest of $\alpha_2$-Adrenergic Agonists and Antagonists in Clinical Practice: Background, Facts and Perspectives, 2007, Curr. Topics Med. Chem. 7:187-194.
Gentili et al., Agonists and Antagonists Targeting the Different $\alpha_2$-Adrenoceptor Subtypes, 2007, Curr. Topics Med. Chem. 7:163-186.
Speake et al., 2-(Anilinomethyl)imidazolines as $\alpha_1$ Adrenergic Receptor Agonists: $\alpha_{1a}$ Subtype Selective 2'-Heteroaryl Compounds, 2003, Bioorganic & Med. Chem. Letters 13:1183-1186.
Pigini et al., Structure-Activity Relationship at $\alpha$-Adrenergic Receptors Within a Series of Imidazoline Analogues of Cirazoline, 2000, Bioorganic & Med. Chem. 8:883-888.
Cross et al., Transdermal Penetration of Vasoconstrictors—Present Understanding and Assessment of the Human Epidermal Flux and Retention of Free Bases and Ion-Pairs, Feb. 2003, Pharma. Res. 20(2):270-274.
Jenni, Information Connection: Tips on Treating Acne, www.mindconnection.com/library/health/acnecare.htm.
Scruggs et al., The Teardrop Sign: A Rare Dermatological Reaction to Brimonidine, 2000, Br. J. Ophthalmol 84:667, Printed Jul. 17, 2007.
Rona's Skin Remedies, Beauty and Style, beauty.ivillage.com/skinbody/facecare/0,,8h9s,00.html.
Peter Lama's Beauty Solutions, Tips for Beautiful Face and Body Skin, Beauty Magazine, www.lamasbeauty.com/beauty/solutions/tips_face_skin.htm, Printed Jul. 17, 2007.
Health Boards, www.healthboards.com/boards/showthread.php?t=5725&highlight=visine+zits, Printed Jul. 17, 2007.
Bratslavsky, DERMAdoctor, Skincare Articles: Your Prescription for Beautiful Skin, www.dermadoctor.com/pages/newsletter221.asp.
ACNE.ORG, www.acne.org/messageboard/index.php?showtopic=34267, Printed Jul. 17, 2007.
ACNETEAM.COM, www.acneteam.com/home-remedies-to-heal-acne-quick.html, Printed Jul. 17, 2007.
Tetrahydrozoline Hydrochloride, www.sigmaaldrich.com/catalog/search/ProductDetail/SIGMA/T4264, Printed Jul. 17, 2007.
Shanler et al., Successful Treatment of the Erythema and Flushing of Rosacea Using a Topically Applied Selective $\alpha_1$-Adrenergic Receptor Agonist, Oxymetazoline, 2007, Arch Dermatol. 143(11):1369-1371.
Leal, Miscellaneous e-mail communication (date unverified).
Issa, "Topical Phenylephrine in Laser in situ Keratomileusis", *Journal Cataract and Refractive Surgery*, Feb. 2007, 33(2): 355-356.
Hong et al., "Effect on Prophylactic Brimonidine Instillation on Bleeding During Strabismus Surgery in Adults", *American Journal of Ophthalmology*, Sep. 2007, 144(3):469-470.
Shah et al., "The Effects of Topical Vitamin K on Bruising After Laser Treatment", *Journal of the American Academy of Dermatology*, Aug. 2002, 47(2):241-244.
Kratz et al., "Controlling Bleeding From Superficial Wounds by the Use of Topical Alpha Adrenoreceptor Agonists Spray—A Randomized, Masked, Controlled Study", *Injury*, Nov. 2004, 35(11):1096-1101.

\* cited by examiner

COMPOSITIONS AND METHODS FOR TREATING PURPURA

CROSS-REFERENCE TO RELATED APPLICATIONS

This application claims priority to U.S. Provisional Application No. 60/988,564 filed on Nov. 16, 2007, which is herein incorporated by reference in its entirety.

GOVERNMENT INTERESTS

Not applicable

PARTIES TO A JOINT RESEARCH AGREEMENT

Not Applicable

INCORPORATION BY REFERENCE OF MATERIAL SUBMITTED ON A COMPACT DISC

Not Applicable

BACKGROUND

1. Field of Invention
Not Applicable
2. Description of Related Art
Not Applicable

BRIEF SUMMARY OF THE INVENTION

Embodiments of the present invention are directed to the use of an α adrenergic agonist for the treatment of vascular extravasation into the skin and particularly for the sequelae manifesting as cutaneous petechiae, purpura or ecchymoses. The α adrenergic agonist may be selected from a selective $\alpha_1$ adrenergic receptor agonist, selective $\alpha_2$ adrenergic receptor agonist, non-selective $\alpha_1/\alpha_2$ adrenergic receptor agonist, agents with $\alpha_2$ adrenergic receptor agonist activity and combinations thereof. The α adrenergic agonist may be administered to a patient in need thereof in a composition comprising a therapeutically effective amount of the α adrenergic agonist, such as a composition for topical administration.

Further embodiments of the present invention are directed to the treatment of purpura in a subject comprising administering a therapeutically effective amount of an α adrenergic agonist to said subject, wherein the purpura is treated. In certain embodiments, the α adrenergic agonist may be selected from a selective $\alpha_1$ adrenergic receptor agonist, selective $\alpha_2$ adrenergic receptor agonist, non-selective $\alpha_1/\alpha_2$ adrenergic receptor agonist, agents with $\alpha_2$ adrenergic receptor agonist activity and combinations thereof. In certain embodiments, the α adrenergic agonist may be administered to a patient in need thereof in a composition comprising a therapeutically effective amount of the α adrenergic agonist. In certain embodiments, the composition may be suitable for topical administration or local administration.

Further embodiments of the present invention are directed to the inhibition of purpura in a subject undergoing a surgical procedure comprising administering a therapeutically effective amount of an α adrenergic agonist to said subject prior to, during or following the surgical procedure, wherein the extent or amount of purpura generated following the surgical procedure is inhibited or decreased. In certain embodiments, the α adrenergic agonist may be selected from a selective $\alpha_1$ adrenergic receptor agonist, selective $\alpha_2$ adrenergic receptor agonist, non-selective $\alpha_1/\alpha_2$ adrenergic receptor agonist, agents with $\alpha_2$ adrenergic receptor agonist activity and combinations thereof. In certain embodiments, the α adrenergic agonist may be administered to a patient in a composition comprising a therapeutically effective amount of the α adrenergic agonist. In certain embodiments, the composition may be suitable for topical administration or local administration.

DESCRIPTION OF DRAWINGS

Not Applicable

DETAILED DESCRIPTION

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

Optical Isomers—Diastereomers—Geometric Isomers—Tautomers. Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The formulas are shown without a definitive stereochemistry at certain positions. The present invention includes all stereoisomers of such formulas and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general formula may be obtained by stereospecific synthesis using optically pure starting materials or reagents of known configuration.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with an $\alpha_1$ or $\alpha_2$ adrenergic receptor agonist or composition thereof, can include, but is not limited to, providing an $\alpha_1$ or $\alpha_2$ adrenergic receptor agonist or composition thereof into or onto the target tissue; or providing an $\alpha_1$ or $\alpha_2$ adrenergic receptor agonist or composition thereof systemically to a patient by, e.g., intravenous injection whereby the therapeutic reaches the target tissue. Administering an $\alpha_1$ or $\alpha_2$ adrenergic receptor agonist or composition thereof may be accomplished by local administration, such as injection directly into or around the site of purpura, topical administration, or by either method in combination with other known techniques The term "improves" is used to convey that the present invention changes either the appearance, form, characteristics and/or the physical attributes of the tissue to which it is being provided, applied or administered. The change in form may be demonstrated by any of the following alone or in combination: enhanced appearance of the skin; decrease in vascular extravasation into the skin; decrease in cutaneous petechiae, purpura or ecchymoses; decrease in pigmentation; and hastening the resolution of the purpuric/hemorrhagic skin lesions.

The term "inhibiting" includes the administration of a compound of the present invention to prevent the onset of the symptoms, alleviating the symptoms, or eliminating the disease, condition or disorder.

The term "patient" and "subject" are interchangeable and may be taken to mean any living organism which may be treated with compounds of the present invention. As such, the terms may include, but are not limited to, any animal, mammal, primate or human, and preferably human.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

By "pharmaceutically acceptable", it is meant the carrier, diluent or excipient must be compatible with the other ingredients of the formulation and not deleterious to the recipient thereof.

"Pharmaceutically acceptable salt" is meant to indicate those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al. (1977) J. Pharm. Sciences, Vol 6. 1-19, describes pharmaceutically acceptable salts in detail.

For the purposes of this invention, a "salt" as used herein is any acid addition salt, preferably a pharmaceutically acceptable acid addition salt, including but not limited to, halogenic acid salts such as, for example, hydrobromic, hydrochloric, hydrofluoric and hydroiodic acid salt; an inorganic acid salt such as, for example, nitric, perchloric, sulfuric and phosphoric acid salt; an organic acid salt such as, for example, sulfonic acid salts (methanesulfonic, trifluoromethan sulfonic, ethanesulfonic, benzenesulfonic or p-toluenesulfonic), acetic, malic, fumaric, succinic, citric, benzoic, gluconic, lactic, mandelic, mucic, pamoic, pantothenic, oxalic and maleic acid salts; and an amino acid salt such as aspartic or glutamic acid salt. The acid addition salt may be a mono- or di-acid addition salt, such as a di-hydrohalogenic, di-sulfuric, di-phosphoric or di-organic acid salt.

Unless otherwise indicated, the term "skin" means that outer integument or covering of the body, consisting of the dermis and the epidermis and resting upon subcutaneous tissue.

As used herein, the term "therapeutic" means an agent utilized to treat, combat, ameliorate, prevent or improve an unwanted condition or disease of a patient. In part, embodiments of the present invention are directed to the treatment of purpura or the decrease in vascular extravasation.

A "therapeutically effective amount" or "effective amount" of a composition is a predetermined amount calculated to achieve the desired effect, i.e., to decrease, block, or reverse purpura. The activity contemplated by the present methods includes both medical therapeutic and/or prophylactic treatment, as appropriate. As used herein, "therapeutically effective amount" refers to the amount of active compound or pharmaceutical agent that elicits a biological or medicinal response in a tissue, system, animal, individual or human that is being sought by a researcher, veterinarian, medical doctor or other clinician, which includes one or more of the following as specified in the particular methodology: (1) preventing the disease; for example, preventing a disease, condition or disorder in an individual that may be predisposed to the disease, condition or disorder but does not yet experience or display the pathology or symptomatology of the disease, (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease, condition or disorder in an individual that is experiencing or displaying the pathology or symptomatology of the disease, condition or disorder (i.e., reducing the severity of the pathology and/or symptomatology). The specific dose of a compound administered according to this invention to obtain therapeutic and/or prophylactic effects will, of course, be determined by the particular circumstances surrounding the case, including, for example, the compound administered, the route of administration, and the condition being treated. The compounds are effective over a wide dosage range and, for example, dosages will normally fall within the range of from about 0.0025% to about 5%, more usually in the range of from about 0.005% to about 2%, more usually in the range of from about 0.05% to about 1%, and more usually in the range of form about 0.1% to about 0.5% by weight. However, it will be understood that the effective amount administered will be determined by the physician in the light of the relevant circumstances including the condition to be treated, the choice of compound to be administered, and the chosen route of administration, and therefore the above dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects.

Generally speaking, the term "tissue" refers to any aggregation of similarly specialized cells which are united in the performance of a particular function.

As used herein, "α adrenergic agonist" refers to an α adrenergic agonist, a prodrug, congener or pharmaceutically acceptable salt thereof and may be selected from a selective $\alpha_1$ adrenergic receptor agonist, selective $\alpha_2$ adrenergic receptor agonist, non-selective $\alpha_1/\alpha_2$ adrenergic receptor agonist, agents with $\alpha_2$ adrenergic receptor agonist activity and combinations thereof. An α adrenergic agonist may be selected from oxymetazoline, naphazoline, tetrahydrozoline, phenylephrine, xylometazoline, methoxamine, metaraminol, midodrine, desglymidodrine, cirazoline, amidephrine, brimonidine, clonidine, guanfacine, guanabenz, apraclonidine, xylazine, medetomidine, dexmedetomidine, α-methyldopa, epinephrine, norepinephrine, isoproterenol, dipivefrin, pseudoephedrine, mephentermine, phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, and tizanidine. Selective $\alpha_1$ adrenergic receptor agonist may be selected from oxymetazoline, naphazoline, tetrahydrozoline, phenylephrine, xylometazoline, methoxamine, metaraminol, midodrine, desglymidodrine, cirazoline, and amidephrine. Selective $\alpha_2$ adrenergic receptor agonist may be selected from brimonidine, clonidine, guanfacine, guanabenz, apraclonidine, xylazine, medetomidine, dexmedetomidine, and α-methyldopa. Non-selective $\alpha_1/\alpha_2$ adrenergic receptor agonist may be selected from epinephrine, norepinephrine, isoproterenol, dipivefrin, pseudoephedrine, and mephentermine. Agents with $\alpha_2$ adrenergic receptor agonist activity may be selected from phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, and tizanidine.

Embodiments of the present invention are directed to the use of an α adrenergic agonist, or pharmaceutically acceptable salt thereof, for the treatment of vascular extravasation into the skin and particularly for the sequelae manifesting as cutaneous petechiae, purpura or ecchymoses. In certain embodiments, the α adrenergic agonist may be selected from a selective $\alpha_1$ adrenergic receptor agonist, selective $\alpha_2$ adrenergic receptor agonist, non-selective $\alpha_1/\alpha_2$ adrenergic receptor agonist, agents with $\alpha_2$ adrenergic receptor agonist activity and a combination thereof. Preferably, the α adrenergic agonist is administered to a patient in a composition, preferably for topical or local administration to a patient in need thereof. In embodiments of the present invention, the α adrenergic agonist may be selected from oxymetazoline, naphazoline, tetrahydrozoline, phenylephrine, xylometazoline, methoxamine, metaraminol, midodrine, desglymidodrine, cirazoline, amidephrine, brimonidine, clonidine, guanfacine, guanabenz, apraclonidine, xylazine, medetomidine, dexmedetomidine, α-methyldopa, epinephrine, norepinephrine, isoproterenol, dipivefrin, pseudoephedrine, mephentermine, phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, tizanidine and combinations thereof. Selective $\alpha_1$ adrenergic receptor agonist may be selected from oxymetazoline, naphazoline, tetrahydrozoline, phenylephrine, xylometazoline, methoxamine, metaraminol, midodrine, desglymidodrine, cirazoline, and amidephrine. In further embodiments, $\alpha_1$-adrenergic receptor agonist is preferably oxymetazoline, naphazoline, tetrahydrozoline, and phenylephrine hydrochloride. Selective $\alpha_2$ adrenergic receptor agonist may be selected from brimonidine, clonidine, guanfacine, guanabenz, apraclonidine, xylazine, medetomidine, dexmedetomidine, and α-methyldopa. In further embodiments, $\alpha_2$-adrenergic receptor agonist is preferably brimonidine. Non-selective $\alpha_1/\alpha_2$ adrenergic receptor agonist may be selected from epinephrine, norepinephrine, isoproterenol, dipivefrin, pseudoephedrine, and mephentermine. Agents with $\alpha_2$ adrenergic receptor agonist activity may be selected from phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, and tizanidine.

Embodiments of the present invention are directed toward the use of composition comprised of an α adrenergic agonist, which may be selected from a selective $\alpha_1$ adrenergic receptor agonist, selective $\alpha_2$ adrenergic receptor agonist, non-selective $\alpha_1/\alpha_2$ adrenergic receptor agonist, agents with $\alpha_2$ adrenergic receptor agonist activity and a combination thereof in a pharmaceutically acceptable carrier in order to treat and improve the cosmetic appearance of these hemorrhagic lesions. In embodiments of the present invention, the α adrenergic agonist may be selected from oxymetazoline, naphazoline, tetrahydrozoline, phenylephrine, xylometazoline, methoxamine, metaraminol, midodrine, desglymidodrine, cirazoline, amidephrine, brimonidine, clonidine, guanfacine, guanabenz, apraclonidine, xylazine, medetomidine, dexmedetomidine, α-methyldopa, epinephrine, norepinephrine, isoproterenol, dipivefrin, pseudoephedrine, mephentermine, phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, tizanidine and combinations thereof. Selective $\alpha_1$ adrenergic receptor agonist may be selected from oxymetazoline, naphazoline, tetrahydrozoline, phenylephrine, xylometazoline, methoxamine, metaraminol, midodrine, desglymidodrine, cirazoline, and amidephrine. In further embodiments, $\alpha_1$-adrenergic receptor agonist is preferably oxymetazoline, naphazoline, tetrahydrozoline, and phenylephrine hydrochloride. Selective $\alpha_2$ adrenergic receptor agonist may be selected from brimonidine, clonidine, guanfacine, guanabenz, apraclonidine, xylazine, medetomidine, dexmedetomidine, and α-methyldopa. In further embodiments, $\alpha_2$-adrenergic receptor agonist is preferably brimonidine. Non-selective $\alpha_1/\alpha_2$ adrenergic receptor agonist may be selected from epinephrine, norepinephrine, isoproterenol, dipivefrin, pseudoephedrine, and mephentermine. Agents with $\alpha_2$ adrenergic receptor agonist activity may be selected from phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, and tizanidine.

As used herein, the term "purpura" refers to any accumulation of blood in the skin due to vascular extravasation, irrespective of size or cause. As used herein, "purpura" refers to medical conditions commonly referred to as "petechiae" (pinpoint spots), "ecchymoses" (larger macular (flat) patches) and "purpura" (larger spots).

Purpura, in general, is hemorrhage of blood out of the vascular spaces and into the surrounding tissues of the skin or mucous membranes. This hemorrhage results in a collection of blood in the dermis of the skin that is visible initially as a dark purple/red discoloration that changes color as it breaks down and is resorbed.

In particular, purpura can be characterized as flat (macular or non-palpable) or raised (palpable or papular). The definition of macular purpuric subtypes include: Petechiae-defined as small purpura (less than 4 millimeters (mm) in diameter, purpura-defined as greater than 4 mm and less than 1 cm (centimeter) in diameter, and ecchymoses-defined as greater than 1 cm in diameter. The size divisions are not absolute but are useful rules of thumb and there is often a range in size of clinical purpuras in any one specific condition.

A bruise, also called a contusion or ecchymosis, is an injury to biological tissue in which the capillaries are damaged, allowing blood to seep into the surrounding tissue. Bruising is usually caused by a blunt impact and its likelihood and its severity increases as one ages due to thinning and loss of elasticity of the skin.

While not wishing to be bound by theory, we believe that by virtue of the fact that these compounds cause local vasoconstriction and a shunting of the blood back to deeper vessels due to their activity at the vascular α adrenergic receptors, their use may decrease the accumulation of blood (and hemosiderin, which is responsible for a long-lasting deep brown color) in the skin, resulting in a cosmetic improvement in these conditions.

Initially classified as either α or β subtype receptors based on anatomical location and functional considerations, in recent years, and with newer molecular genetic techniques, the simple model of two adrenergic receptors (adrenergic receptors) that mediate the vascular response to catecholamines has been replaced. The concept of "generic" α receptors, responsible mostly for "excitatory" functions such as vasoconstriction, uterine and urethral contraction and "generic" β receptors, responsible mostly for "inhibitory" functions such as vasodilatation, bronchodilation, uterine and urethral relaxation (though notably inotropic for the heart) has been further refined and specific receptor subtypes, localizations and functions have been elucidated. The current model is that of a complex family of structurally related receptors consisting of at least six α receptor subtypes ($\alpha_{1A}$ ($\alpha_{1a/c}$), $\alpha_{1B}$, $\alpha_{1D}$, $\alpha_{2A}$ ($\alpha_{2A/D}$), $\alpha_{2B}$, $\alpha_{2C}$) and at least three β receptor subtypes ($\beta_1$, $\beta_2$, $\beta_3$), with additional conformational variants such as $\alpha_{1L}$ and $\beta_4$ bringing the total number of functional adrenergic receptor conformations to at least 11.

These adrenergic receptors are all members of the G-protein-coupled receptor (GPCR) superfamily of proteins and modulate their effects through a classic 7-transmembrane protein second-messenger system. Their final local and systemic effects however are myriad, as noted above, including vasoactive properties ranging from vasoconstriction to vasodilatation and occur through a wide variety of intracellular mechanisms, that are governed by local receptor subtype concentration, relative receptor subtype distribution throughout the body, ligand binding characteristics and other factors (e.g. local temperature, hypoxia). Elegant in vitro, in vivo and ex vivo studies in a variety of vascular tissues and species reveal that the contraction of peripheral vascular smooth muscle is primarily mediated by $\alpha_{1A}$ and $\alpha_{1D}$ receptor subtypes, though does vary somewhat in different vascular regions. $\alpha_2$ receptor studies suggest that $\alpha_{2A/D}$ and $\alpha_{2B}$ effects are also of importance, particularly on the arterial side, and that the $\alpha_{2A/D}$ and $\alpha_{2C}$ effects are of importance on the venular side, though variations based on the experimental model employed are well reported. The actual physiologic and clinical responses to stimulating or inhibiting these receptors selectively is, however, difficult to predict.

Though initially felt to modulate their effects purely through their vasoconstrictive properties, in recent years it has been demonstrated that several of the α vasoconstrictors also exhibit significant anti-inflammatory properties. In upper respiratory tract infections, oxymetazoline and xylometazoline have been shown to inhibit neutrophilic phagocytosis and oxidative burst, resulting in a decrease in microbial killing, decreased generation of pro-inflammatory cytokines, and decreased inflammation. Oxymetazoline has also recently been shown to have significant effects on the arachadonic acid cascade, strongly inhibiting 5-lipoxygenase activity thus decreasing the synthesis of the highly proinflammatory leukotriene $B_4$. A potential clinical role for oxymetazoline, or other agents of this class, as inhibitors of inflammation and oxidative-stress dependent reactions in inflammatory and/or infectious skin conditions is intriguing, but has yet to be investigated.

Further embodiments of the present invention provide methods and compositions for treating purpura and other conditions of the skin characterized by intradermal cutaneous hemorrhages (e.g., petechiae, purpura, ecchymoses) by administering an α adrenergic receptor agonist to a patient in need thereof. In certain embodiments, the α adrenergic agonist may be selected from a selective $\alpha_1$ adrenergic receptor agonist, selective $\alpha_2$ adrenergic receptor agonist, non-selective $\alpha_1/\alpha_2$ adrenergic receptor agonist, agents with $\alpha_2$ adrenergic receptor agonist activity and combinations thereof. In certain embodiments, a therapeutically effective amount of selective $\alpha_1$ adrenergic receptor agonist, selective $\alpha_2$ adrenergic receptor agonist, non-selective $\alpha_1/\alpha_2$ adrenergic receptor agonist, agents with $\alpha_2$ adrenergic receptor agonist activity and combinations thereof is administered. In certain embodiments, the α adrenergic receptor agonist is administered topically or locally to the patient. In embodiments of the present invention, the α adrenergic agonist may be selected from oxymetazoline, naphazoline, tetrahydrozoline, phenylephrine, xylometazoline, methoxamine, metaraminol, midodrine, desglymidodrine, cirazoline, amidephrine, brimonidine, clonidine, guanfacine, guanabenz, apraclonidine, xylazine, medetomidine, dexmedetomidine, α-methyldopa, epinephrine, norepinephrine, isoproterenol, dipivefrin, pseudoephedrine, mephentermine, phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, tizanidine and combinations thereof. Selective $\alpha_1$ adrenergic receptor agonist may be selected from oxymetazoline, naphazoline, tetrahydrozoline, phenylephrine, xylometazoline, methoxamine, metaraminol, midodrine, desglymidodrine, cirazoline, and amidephrine. In further embodiments, $\alpha_1$-adrenergic receptor agonist is preferably oxymetazoline, naphazoline, tetrahydrozoline, and phenylephrine hydrochloride. Selective $\alpha_2$ adrenergic receptor agonist may be selected from brimonidine, clonidine, guanfacine, guanabenz, apraclonidine, xylazine, medetomidine, dexmedetomidine, and α-methyldopa. In further embodiments, $\alpha_2$-adrenergic receptor agonist is preferably brimonidine. Non-selective $\alpha_1/\alpha_2$ adrenergic receptor agonist may be selected from epinephrine, norepinephrine, isoproterenol, dipivefrin, pseudoephedrine, and mephentermine. Agents with $\alpha_2$ adrenergic receptor agonist activity may be selected from phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, and tizanidine.

Another embodiment of the present invention provides methods and compositions for treating other conditions of the skin characterized by intradermal hemorrhage and skin discoloration due to the resorption of the intracutaneous blood accumulation comprising administering an α adrenergic receptor agonist to a patient in need thereof. In certain embodiments, the α adrenergic agonist may be selected from a selective $\alpha_1$ adrenergic receptor agonist, selective $\alpha_2$ adrenergic receptor agonist, non-selective $\alpha_1/\alpha_2$ adrenergic receptor agonist, agents with $\alpha_2$ adrenergic receptor agonist activity and combinations thereof. In certain embodiments, a therapeutically effective amount of the α adrenergic receptor agonist is administered. In certain embodiments, the α adrenergic receptor agonist is administered topically or locally to the patient. In embodiments of the present invention, the α adrenergic agonist may be selected from oxymetazoline, naphazoline, tetrahydrozoline, phenylephrine, xylometazoline, methoxamine, metaraminol, midodrine, desglymidodrine, cirazoline, amidephrine, brimonidine, clonidine, guanfacine, guanabenz, apraclonidine, xylazine, medetomidine, dexmedetomidine, α-methyldopa, epinephrine, norepinephrine, isoproterenol, dipivefrin, pseudoephedrine, mephentermine, phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, tizanidine and combinations thereof. Selective $\alpha_1$ adrenergic receptor agonist may be selected from oxymetazoline, naphazoline, tetrahydrozoline, phenylephrine, xylometazoline, methoxamine, metaraminol, midodrine, desglymidodrine, cirazoline, and amidephrine. In further embodiments, $\alpha_1$-adrenergic receptor agonist is preferably oxymetazoline, naphazoline, tetrahydrozoline, and phenylephrine hydrochloride. Selective $\alpha_2$ adrenergic receptor agonist may be selected from brimonidine, clonidine, guanfacine, guanabenz, apraclonidine, xylazine, medetomidine, dexmedetomidine, and α-methyldopa. In further embodiments, $\alpha_2$-adrenergic receptor agonist is preferably brimonidine. Non-selective $\alpha_1/\alpha_2$ adrenergic receptor agonist may be selected from epinephrine, norepinephrine, isoproterenol, dipivefrin, pseudoephedrine, and mephentermine. Agents with $\alpha_2$ adrenergic receptor agonist activity may be selected from phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, and tizanidine.

Another embodiment of the present invention provides methods and compositions for improvement of bruising comprising administering an α adrenergic receptor agonist to a patient in need thereof. In certain embodiments, the α adrenergic agonist may be selected from a selective $\alpha_1$ adrenergic receptor agonist, selective $\alpha_2$ adrenergic receptor agonist, non-selective $\alpha_1/\alpha_2$ adrenergic receptor agonist, agents with $\alpha_2$ adrenergic receptor agonist activity and combinations thereof. In certain embodiments, a therapeutically effective amount of the α adrenergic receptor agonist is administered. In certain embodiments, the α adrenergic receptor agonist is administered topically or locally to the patient. In embodiments of the present invention, the α adrenergic agonist may be selected from oxymetazoline, naphazoline, tetrahydrozoline, phenylephrine, xylometazoline, methoxamine, metaraminol, midodrine, desglymidodrine, cirazoline, amidephrine, brimonidine, clonidine, guanfacine, guanabenz, apraclonidine, xylazine, medetomidine, dexmedetomidine, α-methyldopa, epinephrine, norepinephrine, isoproterenol, dipivefrin, pseudoephedrine, mephentermine, phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, tizanidine and combinations thereof. Selective $\alpha_1$ adrenergic receptor agonist may be selected from oxymetazoline, naphazoline, tetrahydrozoline, phenylephrine, xylometazoline, methoxamine, metaraminol, midodrine, desglymidodrine, cirazoline, and amidephrine. In further embodiments, $\alpha_1$-adrenergic receptor agonist is preferably oxymetazoline, naphazoline, tetrahydrozoline, and phenylephrine hydrochloride. Selective $\alpha_2$ adrenergic receptor agonist may be selected from brimonidine, clonidine, guanfacine, guanabenz, apraclonidine, xylazine, medetomidine, dexmedetomidine, and α-methyldopa. In further embodiments, $\alpha_2$-adrenergic receptor agonist is preferably brimonidine. Non-selective $\alpha_1/\alpha_2$ adrenergic receptor agonist may be selected from epinephrine, norepinephrine, isoproterenol, dipivefrin, pseudoephedrine, and mephentermine. Agents with $\alpha_2$ adrenergic receptor agonist activity may be selected from phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, and tizanidine.

Other embodiments of the present invention are methods and compositions for treating the cutaneous manifestations of intrinsic (chronological) and extrinsic (e.g. caused by sun exposure, smoking, etc) aging of the skin including, but not limited to, purpura (or "bruising"), skin wrinkling, sallow-yellow skin discoloration, dark circles under the eyes, bruising, bruising caused by laser administration, and hyperpigmentation comprising administering an α adrenergic receptor agonist to a patient in need thereof. In certain embodiments, the α adrenergic agonist may be selected from a selective $\alpha_1$ adrenergic receptor agonist, selective $\alpha_2$ adrenergic receptor agonist, non-selective $\alpha_1/\alpha_2$ adrenergic receptor agonist, agents with $\alpha_2$ adrenergic receptor agonist activity and combinations thereof. In certain embodiments, a therapeutically effective amount of the α adrenergic receptor agonist is administered. In certain embodiments, the α adrenergic receptor agonist is administered topically or locally to the patient. In embodiments of the present invention, the α adrenergic agonist may be selected from oxymetazoline, naphazoline, tetrahydrozoline, phenylephrine, xylometazoline, methoxamine, metaraminol, midodrine, desglymidodrine, cirazoline, amidephrine, brimonidine, clonidine, guanfacine, guanabenz, apraclonidine, xylazine, medetomidine, dexmedetomidine, α-methyldopa, epinephrine, norepinephrine, isoproterenol, dipivefrin, pseudoephedrine, mephentermine, phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, tizanidine and combinations thereof. Selective $\alpha_1$ adrenergic receptor agonist may be selected from oxymetazoline, naphazoline, tetrahydrozoline, phenylephrine, xylometazoline, methoxamine, metaraminol, midodrine, desglymidodrine, cirazoline, and amidephrine. In further embodiments, $\alpha_1$-adrenergic receptor agonist is preferably oxymetazoline, naphazoline, tetrahydrozoline, and phenylephrine hydrochloride. Selective $\alpha_2$ adrenergic receptor agonist may be selected from brimonidine, clonidine, guanfacine, guanabenz, apraclonidine, xylazine, medetomidine, dexmedetomidine, and α-methyldopa. In further embodiments, $\alpha_2$-adrenergic receptor agonist is preferably brimonidine. Non-selective $\alpha_1/\alpha_2$ adrenergic receptor agonist may be selected from epinephrine, norepinephrine, isoproterenol, dipivefrin, pseudoephedrine, and mephentermine. Agents with $\alpha_2$ adrenergic receptor agonist activity may be selected from phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, and tizanidine.

Further embodiment of the present invention provides methods and compositions for decreasing bruising caused by laser by administering an α adrenergic receptor agonist to a patient in need thereof prior to or soon after laser treatment. In certain embodiments, the α adrenergic agonist may be selected from a selective $\alpha_1$ adrenergic receptor agonist, selective $\alpha_2$ adrenergic receptor agonist, non-selective $\alpha_1/\alpha_2$ adrenergic receptor agonist, agents with $\alpha_2$ adrenergic receptor agonist activity and combinations thereof. In certain embodiments, a therapeutically effective amount of the α adrenergic receptor agonist is administered. In certain embodiments, the α adrenergic receptor agonist is administered topically or locally to the patient. In embodiments of the present invention, the α adrenergic agonist may be selected from oxymetazoline, naphazoline, tetrahydrozoline, phenylephrine, xylometazoline, methoxamine, metaraminol, midodrine, desglymidodrine, cirazoline, amidephrine, brimonidine, clonidine, guanfacine, guanabenz, apraclonidine, xylazine, medetomidine, dexmedetomidine, α-methyldopa, epinephrine, norepinephrine, isoproterenol, dipivefrin, pseudoephedrine, mephentermine, phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, tizanidine and combinations thereof. Selective $\alpha_1$ adrenergic receptor agonist may be selected from oxymetazoline, naphazoline, tetrahydrozoline, phenylephrine, xylometazoline, methoxamine, metaraminol, midodrine, desglymidodrine, cirazoline, and amidephrine. In further embodiments, $\alpha_1$-adrenergic receptor agonist is preferably oxymetazoline, naphazoline, tetrahydrozoline, and phenylephrine hydrochloride. Selective $\alpha_2$ adrenergic receptor agonist may be selected from brimonidine, clonidine, guanfacine, guanabenz, apraclonidine, xylazine, medetomidine, dexmedetomidine, and α-methyldopa. In further embodiments, $\alpha_2$-adrenergic receptor agonist is preferably brimonidine. Non-selective $\alpha_1/\alpha_2$ adrenergic receptor agonist may be selected from epinephrine, norepinephrine, isoproterenol, dipivefrin, pseudoephedrine, and mephentermine. Agents with $\alpha_2$ adrenergic receptor agonist activity may be selected from phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, and tizanidine.

Further embodiments of the present invention provide methods and compositions for resolving purpura using such a laser or a non-laser light source in combination with an $\alpha_1$ adrenergic receptor agonist, an $\alpha_2$ adrenergic receptor agonist or a combination thereof to a patient in need thereof prior to, during or following the use of such a laser. In certain embodiments, the α adrenergic agonist may be selected from a selective $\alpha_1$ adrenergic receptor agonist, selective $\alpha_2$ adrenergic receptor agonist, non-selective $\alpha_1/\alpha_2$ adrenergic receptor agonist, agents with $\alpha_2$ adrenergic receptor agonist activity and combinations thereof. In certain embodiments, a therapeutically effective amount of the α adrenergic receptor agonist is administered. In certain embodiments, the α adrenergic receptor agonist is administered topically or locally to the patient. In embodiments of the present invention, the α adrenergic agonist may be selected from oxymetazoline, naphazoline, tetrahydrozoline, phenylephrine, xylometazoline, methoxamine, metaraminol, midodrine, desglymidodrine, cirazoline, amidephrine, brimonidine, clonidine, guanfacine, guanabenz, apraclonidine, xylazine, medetomidine, dexmedetomidine, α-methyldopa, epinephrine, norepinephrine, isoproterenol, dipivefrin, pseudoephedrine, mephentermine, phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, tizanidine and combinations thereof. Selective $\alpha_1$ adrenergic receptor agonist may be selected from oxymetazoline, naphazoline, tetrahydrozoline, phenylephrine, xylometazoline, methoxamine, metaraminol, midodrine, desglymidodrine, cirazoline, and amidephrine. In further embodiments, $\alpha_1$-adrenergic receptor agonist is preferably oxymetazoline, naphazoline, tetrahydrozoline, and phenylephrine hydrochloride. Selective $\alpha_2$ adrenergic receptor agonist may be selected from brimonidine, clonidine, guanfacine, guanabenz, apraclonidine, xylazine, medetomidine, dexmedetomidine, and α-methyldopa. In further embodiments, $\alpha_2$-adrenergic receptor agonist is preferably brimonidine. Non-selective $\alpha_1/\alpha_2$ adrenergic receptor agonist may be selected from epinephrine, norepinephrine, isoproterenol, dipivefrin, pseudoephedrine, and mephentermine. Agents with $\alpha_2$ adrenergic receptor agonist activity may be selected from phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, and tizanidine.

Further embodiments of the present invention provide methods and compositions for treatment of purpura conditions caused by a surgical procedure involving physical trauma to the skin and/or cutaneous vasculature. As used herein, the term surgical procedure refers to any intervention that may result in an injury to biological tissue in which the skin, cutaneous and subcutaneous vascular and surrounding tissues might sustain injury that would allow blood to seep into the surrounding tissue. Such interventions include, but are not limited to needle-sticks (e.g. for phlebotomy or infusion), injection of therapeutic agents (e.g. vaccines or sclerotherapy, injection of neurotoxins or fillers for soft-tissue augmentation, cold-steel surgery (e.g. "incisional" or "excisional" surgery), "minimally-invasive" procedures (e.g. laparoscopic, arthroscopic procedures, liposuction), laser, thermal, intense pulsed light (IPL), other electromagnetic radiation-based procedures, radiofrequency, chemical, electro-surgical and ultrasonic procedures. In such embodiments, a therapeutically effective amount of the α adrenergic receptor agonist, is administered to a patient prior to, during and/or after said surgical procedure, such that the formation of purpura (extent, duration, amount, size) is inhibited or decreased. In certain embodiments, the α adrenergic agonist may be selected from a selective $\alpha_1$ adrenergic receptor agonist, selective $\alpha_2$ adrenergic receptor agonist, non-selective $\alpha_1/\alpha_2$ adrenergic receptor agonist, agents with $\alpha_2$ adrenergic receptor agonist activity and combinations thereof. In certain embodiments, a therapeutically effective amount of the α adrenergic receptor agonist is administered. In certain embodiments, the α adrenergic receptor agonist is administered topically or locally to the patient. In embodiments of the present invention, the α adrenergic agonist may be selected from oxymetazoline, naphazoline, tetrahydrozoline, phenylephrine, xylometazoline, methoxamine, metaraminol, midodrine, desglymidodrine, cirazoline, amidephrine, brimonidine, clonidine, guanfacine, guanabenz, apraclonidine, xylazine, medetomidine, dexmedetomidine, α-methyldopa, epinephrine, norepinephrine, isoproterenol, dipivefrin, pseudoephedrine, mephentermine, phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, tizanidine and combinations thereof. Selective $\alpha_1$ adrenergic receptor agonist may be selected from oxymetazoline, naphazoline, tetrahydrozoline, phenylephrine, xylometazoline, methoxamine, metaraminol, midodrine, desglymidodrine, cirazoline, and amidephrine. In further embodiments, $\alpha_1$-adrenergic receptor agonist is preferably oxymetazoline, naphazoline, tetrahydrozoline, and phenylephrine hydrochloride. Selective $\alpha_2$ adrenergic receptor agonist may be selected from brimonidine, clonidine, guanfacine, guanabenz, apraclonidine, xylazine, medetomidine, dexmedetomidine, and α-methyldopa. In further embodiments, $\alpha_2$-adrenergic receptor agonist is preferably brimonidine. Non-selective $\alpha_1/\alpha_2$ adrenergic receptor agonist may be selected from epinephrine, norepinephrine, isoproterenol, dipivefrin, pseudoephedrine, and mephentermine. Agents with $\alpha_2$ adrenergic receptor agonist activity may be selected from phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, and tizanidine.

Further embodiments of the present invention provide methods and compositions for preventing purpura caused by a surgical procedure involving physical trauma to the skin and/or cutaneous vasculature, such as, for example, external blunt-force trauma, internal blunt-force trauma (e.g. liposuction trauma or surgical undermining trauma), "sharp" trauma (e.g. skin incision, skin puncture, needle stick), laceration, dermabrasion, chemical burn, thermal burn, and electrical burn. In such embodiments, a therapeutically effective amount of the α adrenergic receptor agonist, is administered to a patient prior to, during and/or after said surgical procedure, such that the formation of purpura (extent, duration, amount, size) is prevented. In certain embodiments, the α adrenergic agonist may be selected from a selective $\alpha_1$ adrenergic receptor agonist, selective $\alpha_2$ adrenergic receptor agonist, non-selective $\alpha_1/\alpha_2$ adrenergic receptor agonist, agents with $\alpha_2$ adrenergic receptor agonist activity and combinations thereof. In certain embodiments, a therapeutically effective amount of the α adrenergic receptor agonist is administered. In certain embodiments, the α adrenergic receptor agonist is administered topically or locally to the patient. In embodiments of the present invention, the α adrenergic agonist may be selected from oxymetazoline, naphazoline, tetrahydrozoline, phenylephrine, xylometazoline, methoxamine, metaraminol, midodrine, desglymidodrine, cirazoline, amidephrine, brimonidine, clonidine, guanfacine, guanabenz, apraclonidine, xylazine, medetomidine, dexmedetomidine, α-methyldopa, epinephrine, norepinephrine, isoproterenol, dipivefrin, pseudoephedrine, mephentermine, phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, tizanidine and combinations thereof. Selective $\alpha_1$ adrenergic receptor agonist may be selected from oxymetazoline, naphazoline, tetrahydrozoline, phenylephrine, xylometazoline, methoxamine, metaraminol, midodrine, desglymidodrine, cirazoline, and amidephrine. In further embodiments, $\alpha_1$-adrenergic receptor agonist is preferably oxymetazoline, naphazoline, tetrahydrozoline, and phenylephrine hydrochloride. Selective $\alpha_2$ adrenergic receptor agonist may be selected from brimonidine, clonidine, guanfacine, guanabenz, apraclonidine, xylazine, medetomidine, dexmedetomidine, and α-methyldopa. In further embodiments, $\alpha_2$-adrenergic receptor agonist is preferably brimonidine. Non-selective $\alpha_1/\alpha_2$ adrenergic receptor agonist may be selected from epinephrine, norepinephrine, isoproterenol, dipivefrin, pseudoephedrine, and mephentermine. Agents with $\alpha_2$ adrenergic receptor agonist activity may be selected from phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, and tizanidine.

Further embodiments of the present invention provide compositions comprising at least one $\alpha_1$ adrenergic receptor agonist and/or at least one $\alpha_2$ adrenergic receptor agonist, alone or in combination, into a cosmetic, pharmaceutical or dermatological composition for decreasing and/or preventing purpura and other conditions of the skin characterized by intradermal cutaneous hemorrhages and to administer said compositions to a mammal, notably a human, in order to treat or prevent the disease states indicated above.

Further embodiments of the present invention provide compositions comprising at an α adrenergic receptor agonist in a cosmetic, pharmaceutical or dermatological composition for decreasing and/or preventing purpura and other conditions of the skin characterized by intradermal cutaneous hemorrhages. In certain embodiments, the α adrenergic receptor agonist may be selected from a selective $\alpha_1$ adrenergic receptor agonist, selective $\alpha_2$ adrenergic receptor agonist, non-selective $\alpha_1/\alpha_2$ adrenergic receptor agonist, agents with $\alpha_2$ adrenergic receptor agonist activity and combinations thereof. In some embodiments, the composition may further comprise other agents known to be effective in treating purpura.

Embodiments of the present invention are directed to methods for treating purpura and other conditions of the skin characterized by intradermal cutaneous hemorrhages in a patient in need of such treatment, comprising the administration, preferably topical or local, of a therapeutically effective amount of a composition comprising an α-adrenergic receptor agonist. In certain embodiments, the α adrenergic agonist may be selected from a selective $\alpha_1$ adrenergic receptor agonist, selective $\alpha_2$ adrenergic receptor agonist, non-selective $\alpha_1/\alpha_2$ adrenergic receptor agonist, agents with $\alpha_2$ adrenergic receptor agonist activity and combinations thereof.

In embodiments of the present invention, the α adrenergic agonist may be selected from oxymetazoline, naphazoline, tetrahydrozoline, phenylephrine, xylometazoline, methoxamine, metaraminol, midodrine, desglymidodrine, cirazoline, amidephrine, brimonidine, clonidine, guanfacine, guanabenz, apraclonidine, xylazine, medetomidine, dexmedetomidine, α-methyldopa, epinephrine, norepinephrine, isoproterenol, dipivefrin, pseudoephedrine, mephentermine, phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, tizanidine and combinations thereof.

Selective $\alpha_1$ adrenergic receptor agonist may be selected from oxymetazoline, naphazoline, tetrahydrozoline, phenylephrine, xylometazoline, methoxamine, metaraminol, midodrine, desglymidodrine, cirazoline, and amidephrine. In further embodiments, $\alpha_1$-adrenergic receptor agonist is preferably oxymetazoline, naphazoline, tetrahydrozoline, and phenylephrine hydrochloride.

Selective $\alpha_2$ adrenergic receptor agonist may be selected from brimonidine, clonidine, guanfacine, guanabenz, apraclonidine, xylazine, medetomidine, dexmedetomidine, and α-methyldopa. In further embodiments, $\alpha_2$-adrenergic receptor agonist is preferably brimonidine.

Non-selective $\alpha_1/\alpha_2$ adrenergic receptor agonist may be selected from epinephrine, norepinephrine, isoproterenol, dipivefrin, pseudoephedrine, and mephentermine.

Agents with $\alpha_2$ adrenergic receptor agonist activity may be selected from phenylpropanolamine, propylhexadrine, amphetamine, dextroamphetamine, ephedrine, epinine (deoxyepinephrine), ethylnorepinephrine, levarterenol (L-Norepinephrine), lofexidine, methamphetamine, α-methylnorepinephrine, methylphenidate, mivazerol, moxonidine, norepinephrine, norphenylephrine, pemoline, and tizanidine.

Preferably, the composition comprises at least one selective $\alpha_1$ adrenergic receptor agonist, selective $\alpha_2$ adrenergic receptor agonist, non-selective $\alpha_1/\alpha_2$ adrenergic receptor agonist, and agents with $\alpha_2$ adrenergic receptor agonist activity formulated in a pharmaceutically acceptable medium. For example, a gel, cream, lotion or solution which may be administered by spreading the gel, cream, lotion or solution onto or surrounding the affected area.

Other embodiments may also include combinations of therapeutically effective amounts of combinations of a selective $\alpha_1$ adrenergic receptor agonist, a selective $\alpha_2$ adrenergic receptor agonist, a non-selective $\alpha_1/\alpha_2$ adrenergic receptor agonist, and agents with $\alpha_2$ adrenergic receptor agonist activity. The therapeutically effective amount of each agent may be significantly decreased when used in combination with other α-adrenergic receptor agonist than when used as the sole active agent.

Preferred embodiments may also include enhancers of cutaneous penetration or inhibitors or regulators of cutaneous penetration as required to increase therapeutic efficacy and/or decrease systemic absorption and any potential undesirable systemic effects of the active agent(s).

Further embodiments of the present invention provide methods of treating such conditions by administering one or more $\alpha_1$-adrenergic receptor agonists alone or in combination with one or more and $\alpha_2$-adrenergic receptor agonists (alone or in combination) with active agents for preventing and/or treating other skin complaints, conditions and afflictions. Examples of these agents include: (i) antirosacea agents such as metronidazole, precipitated sulfur, sodium sulfacetamide, or azelaic acid; (ii) antibacterial agents (antibiotics) such as clindamycin phosphate, erythromycin, or antibiotics from the tetracycline family; (iii) antimycobacterial agents such as dapsone; (iv) antiacne agents such as retinoids, or benzoyl peroxide; (v) antiparasitic agents such as metronidazole, permethrin, crotamiton or pyrethroids; (vi) antifungal agents such as compounds of the imidazole family such as miconazole, clotrimazole, econazole, ketoconazole, or salts thereof, polyene compounds such as amphotericin B, compound of the allylamine family such as terbinafine; (vii) steroidal anti-inflammatory agents such as hydrocortisone triamcinolone, fluocinonide, betamethasone valerate or clobetasol propionate, or non-steroidal anti-inflammatory agents such as ibuprofen and salts thereof, naproxen and salts thereof, or acetaminophen; (viii) anesthetic agents such as lidocaine, prilocaine, tetracaine, hydrochloride and derivatives thereof; (ix) antipruriginous agents such as thenaldine, trimeprazine, or pramoxine; (x) antiviral agents such as acyclovir; (xi) keratolytic agents such as alpha- and beta-hydroxy acids such as glycolic acid or salicylic acid, or urea; (xii) anti-free radical agents (antioxidants) such as vitamin E (alpha tocopherol) and its derivatives, vitamin C (ascorbic acid), vitamin A (retinol) and its derivatives, vitamin K, superoxide dismutase and derivatives of plants, particularly of the genus *Arnica*, such as sesquiterpene lactones (xiii) antiseborrheic agents such as zinc pyrithione and selenium sulfide; (xiv) antihistamines such as cyproheptadine or hydroxyzine; (xv) tricyclic antidepressants such as doxepin hydrochloride and (xvi) combinations thereof.

For example, in some aspects, the invention is directed to a pharmaceutical composition comprising a selective $\alpha_1$ adrenergic receptor agonist, a selective $\alpha_2$ adrenergic receptor agonist, a non-selective $\alpha_1/\alpha_2$ adrenergic receptor agonist, agents with $\alpha_2$ adrenergic receptor agonist activity and combinations thereof and a pharmaceutically acceptable carrier or diluent, or an effective amount of a pharmaceutical composition comprising a compound as defined above.

The compositions may be formulated to be administered orally, ophthalmically, intravenously, intramuscularly, intraarterially, intramedularry, intrathecally, intraventricularly, transdermally, subcutaneously, intraperitoneally, intravesicularly, intranasally, eternally, topically, sublingually, or rectally, preferably topically or locally.

Embodiments of the invention include compositions comprising an α adrenergic receptor agonist, preferably a selective $\alpha_1$ adrenergic receptor agonist, a selective $\alpha_2$ adrenergic receptor agonist, a non-selective $\alpha_1/\alpha_2$ adrenergic receptor agonist, agents with $\alpha_2$ adrenergic receptor agonist activity and combinations thereof. Preferably the compositions may be administered topically or locally. The compounds of the present invention can be administered in the conventional manner by any route where they are active. Administration can be systemic, topical, or oral. For example, administration can be, but is not limited to, parenteral, subcutaneous, intravenous, intramuscular, intraperitoneal, transdermal, oral, buccal, or ocular routes, or intravaginally, intravesicularly, by inhalation, by depot injections, or by implants. Thus, modes of administration for the compounds of the present invention (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

One of ordinary skill in the art will understand and appreciate the dosages and timing of said dosages to be administered to a patient in need thereof. The doses and duration of treatment may vary, and may be based on assessment by one of ordinary skill in the art based on monitoring and measuring improvements in skin tissues. This assessment may be made based on outward physical signs of improvement, such as decreased redness, or other physiological signs or markers. The doses may also depend on the condition or disease being treated, the degree of the condition or disease being treated and further on the age and weight of the patient.

Specific modes of administration will depend on the indication. The selection of the specific route of administration and the dose regimen may be adjusted or titrated by the clinician according to methods known to the clinician in order to obtain the optimal clinical response. The amount of compound to be administered may be that amount which is therapeutically effective. The dosage to be administered may depend on the characteristics of the subject being treated, e.g., the particular animal or human subject treated, age, weight, health, types of concurrent treatment, if any, and frequency of treatments, and can be easily determined by one of skill in the art (e.g., by the clinician).

A preferable route of administration of the compositions of the present invention may be topical or local.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or acetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Pharmaceutical formulations comprising the compounds of the present invention and a suitable carrier may also be any number of solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and Goodman & Gilman's *The Pharmaceutical Basis of Therapeutics*, 6th Edition, MacMillan Publishing Co., New York (1980) can be consulted.

The compounds of the present invention can be formulated for parenteral administration by injection, e.g., by bolus injection or continuous infusion. The compounds can be administered by continuous infusion over a period of about 15 minutes to about 24 hours. Formulations for injection can be presented in unit dosage form, e.g., in ampoules or in multidose containers, with an added preservative. The compositions can take such forms as suspensions, solutions or emulsions in oily or aqueous vehicles, and can contain formulatory agents such as suspending, stabilizing and/or dispersing agents.

For oral administration, the compounds can be formulated readily by combining these compounds with pharmaceutically acceptable carriers well known in the art. As used herein, the term "pharmaceutically acceptable carrier" means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Syrups and elixirs may be formulated with sweetening agents, for example glycerol, propylene glycol, sorbitol or sucrose. Such formulations may also contain a demulcent, a preservative and flavoring and coloring agents.

For buccal or sublingual administration, the compositions can take the form of tablets, flash melts or lozenges formulated in any conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds of the present invention can also be formulated in rectal compositions such as suppositories or retention enemas, e.g., containing conventional suppository bases such as cocoa butter or other glycerides.

In addition to the formulations described previously, the compounds of the present invention can also be formulated as a depot preparation. Such long acting formulations can be administered by implantation (for example subcutaneously or intramuscularly) or by intramuscular injection.

Depot injections can be administered at about 1 to about 6 months or longer intervals. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

In transdermal administration, the compounds of the present invention, for example, can be applied to a plaster, or can be applied by transdermal, therapeutic systems that are consequently supplied to the organism.

Pharmaceutical and therapeutic compositions of the compounds also can comprise suitable solid or gel phase carriers or excipients. Examples of such carriers or excipients include, but are not limited to, calcium carbonate, calcium phosphate, various sugars, starches, cellulose derivatives, gelatin, and polymers such as, e.g., polyethylene glycols.

Although the present invention has been described in considerable detail with reference to certain preferred embodiments thereof, other versions are possible. Therefore the spirit and scope of the appended claims should not be limited to the description and the preferred versions contained within this specification.

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and do not limit the scope of the invention. Various modifications and combinations of the illustrative embodiments, as well as other embodiments of the invention, will be apparent to persons skilled in the art upon reference to the description.

Example 1

In order to evaluate the effect of topically applied $\alpha_1$ and $\alpha_2$ adrenergic agonists on the resolution of purpura, purpuric macules/patches were experimentally created on the trunk of a volunteer. Seven sites were marked, and utilizing a pulsed-dye laser (585 nm) and laser light parameters known to be purpurogenic, purpuric macules/patches were successfully induced at each site. Immediately after the laser energy was delivered, the topical application of commercially available $\alpha_1$ and/or $\alpha_2$ adrenergic agonist preparations was begun. The preparations were applied to the skin and gently rubbed on the skin over and immediately surrounding the laser treatment sites every 6-8 hours (3-4 times/day). The applied solution was allowed to air-dry without any dressing. The areas were followed clinically and photographically. The evaluated compounds were:

Site 1: Oxymetazoline hydrochloride (0.05%): A solution of oxymetazoline hydrochloride 0.05% (Afrin® Original 12 Hour Nasal Spray (Schering-Plough Healthcare Products) containing: oxymetazoline hydrochloride 0.05%, benzalkonium chloride solution, edetate disodium, polyethylene glycol, povidone, propylene glycol, purified water, sodium phosphate dibasic, sodium phosphate monobasic.

Site 2: Naphazoline hydrochloride (0.03%): A solution of naphazoline hydrochloride 0.03% (Clear Eyes® Maximum Redness Relief (Prestige Brands Inc.) containing: naphazoline hydrochloride 0.03%, glycerin 0.5%, benzalkonium chloride, boric acid, edetate disodium, purified water, sodium borate).

Site 3: Tetrahydrozoline hydrochloride (0.05%): A solution of tetrahydrozoline hydrochloride 0.05% (Visine® Original (Pfizer Consumer Healthcare) containing: tetrahydrozoline hydrochloride 0.05%, benzalkonium chloride, boric acid, edetate disodium, purified water, sodium borate, sodium chloride).

Site 4: Phenylephrine hydrochloride (1.0%): A solution of phenylephrine hydrochloride 1.0% (Neo-Synephrine® Extra Strength Spray (Bayer HealthCare) containing: phenylephrine hydrochloride 1.0%, anhydrous citric acid, benzalkonium chloride, sodium chloride, sodium citrate, water).

Site 5: Brimonidine tartrate (0.2%): A solution of brimonidine tartrate 0.2% (Bausch & Lomb Inc.) containing: brimonidine tartrate 0.02%, citric acid, polyvinyl alcohol, sodium chloride, sodium citrate, purified water, benzalkonium chloride (0.005%).

Site 6: Oxymetazoline hydrochloride 0.05% and brimonidine tartrate 0.2%: The solution of oxymetazoline hydrochloride 0.05% (Afrin® (Original 12 Hour Nasal Spray (Schering-Plough Healthcare Products) containing: oxymetazoline hydrochloride 0.05%, benzalkonium chloride solution, edetate disodium, polyethylene glycol, povidone, propylene glycol, purified water, sodium phosphate dibasic, sodium phosphate monobasic was applied first, then was followed by the application of the solution of brimonidine tartrate 0.2% (Bausch & Lomb Inc.) containing: brimonidine tartrate 0.02%, citric acid, polyvinyl alcohol, sodium chloride, sodium citrate, purified water, benzalkonium chloride (0.005%).

Site 7: No treatment after laser light delivered. ("Control")

The sites were followed clinically and photographically 1, 3, 4, 6, 11 and 13 days after the creation of the purpura. In each of the sites treated with at least one of the α agonist preparations, the resolution of the purpura was more rapid than in the non-treated control site. This effect was most pronounced on site 2 (naphazoline 0.03%), site 4 (phenylephrine 1.0%), site 1 (oxymetazoline 0.05%), and site 6 (oxymetazoline hydrochloride 0.05%+brimonidine tartrate 0.2%). No local or systemic side effects were noted, and in particular, there was no rebound erythema or edema noted.

These trials demonstrate that selective $\alpha_1$ adrenergic receptor agonists and selective $\alpha_2$ adrenergic receptor agonists, used separately or in combination, when topically applied to and around a treatment site after a procedure that can/will induce purpura, will reduce the size and appearance of the purpuric macules/patches and is an effective treatment to hasten their resolution.

Example 2

In order to evaluate the effect of topically applied $\alpha_1$ and $\alpha_2$ adrenergic agonists on the prevention of laser-induced purpura on normal non-actinically damaged skin, seven sites on the trunk of a volunteer were marked and treated with the topical application of a commercially available $\alpha_1$ and/or $\alpha_2$ agonist preparation. Six (of the seven) marked sites were pretreated with the topical application of at least one of the testing preparations. The preparations were applied to the skin and gently rubbed on the skin over and immediately surrounding the laser treatment sites 3 hours prior to and 1 hour prior to the delivery of the laser energy. The applied solution was allowed to air-dry without any dressing. Utilizing a pulsed-dye laser (585 nm) and laser light parameters known to be purpurogenic, purpuric macules/patches were successfully induced at each site. After the delivery of the laser energy, each spot received only topical petrolatum jelly 3-4 times/day and no additional application of any testing compound. The sites were followed clinically and photographically 1, 3, 4, 6, 11 and 13 days after the creation of the purpura. The evaluated compounds were:

Site 8: Oxymetazoline hydrochloride (0.05%): A solution of oxymetazoline hydrochloride 0.05% (Afrin® Original 12 Hour Nasal Spray (Schering-Plough Healthcare Products) containing: oxymetazoline hydrochloride 0.05%, benzalkonium chloride solution, edetate disodium, polyethylene glycol, povidone, propylene glycol, purified water, sodium phosphate dibasic, sodium phosphate monobasic.

Site 9: Naphazoline hydrochloride (0.03%): A solution of naphazoline hydrochloride 0.03% (Clear Eyes® Maximum Redness Relief (Prestige Brands Inc.) containing: naphazoline hydrochloride 0.03%, glycerin 0.5%, benzalkonium chloride, boric acid, edetate disodium, purified water, sodium borate).

Site 10: Tetrahydrozoline hydrochloride (0.05%): A solution of tetrahydrozoline hydrochloride 0.05% (Visine® Original (Pfizer Consumer Healthcare) containing: tetrahydrozoline hydrochloride 0.05%, benzalkonium chloride, boric acid, edetate disodium, purified water, sodium borate, sodium chloride).

Site 11: Phenylephrine hydrochloride (1.0%): A solution of phenylephrine hydrochloride 1.0% (Neo-Synephrine® Extra Strength Spray (Bayer HealthCare) containing: phenylephrine hydrochloride 1.0%, anhydrous citric acid, benzalkonium chloride, sodium chloride, sodium citrate, water).

Site 12: Brimonidine tartrate (0.2%): A solution of brimonidine tartrate 0.2% (Bausch & Lomb Inc.) containing: brimonidine tartrate 0.02%, citric acid, polyvinyl alcohol, sodium chloride, sodium citrate, purified water, benzalkonium chloride (0.005%).

Site 13: oxymetazoline hydrochloride 0.05% and brimonidine tartrate 0.2%: The solution of oxymetazoline hydrochloride 0.05% (Afrin® Original 12 Hour Nasal Spray (Schering-Plough Healthcare Products) containing: oxymetazoline hydrochloride 0.05%, benzalkonium chloride solution, edetate disodium, polyethylene glycol, povidone, propylene glycol, purified water, sodium phosphate dibasic, sodium phosphate monobasic was applied first, then was followed by the application of the solution of brimonidine tartrate 0.2% (Bausch & Lomb Inc.) containing: brimonidine tartrate 0.02%, citric acid, polyvinyl alcohol, sodium chloride, sodium citrate, purified water, benzalkonium chloride (0.005%).

Site 14: No treatment after laser light delivered. ("Control")

In each of the sites treated with at least one of the α agonist preparations prior to the delivery of the laser energy, the purpuric macule/patch created was smaller than in the non pre-treated site. The time course of the resolution of the purpura was shortened as well. This effect was more pronounced on the sites pretreated with oxymetazoline hydrochloride 0.05%, naphazoline hydrochloride 0.03%, tetrahydrozoline hydrochloride 0.05%, and phenylephrine hydrochloride 1.0%, and was observed, though less pronounced, on the site pretreated with brimonidine tartrate 0.2% alone, and the site pretreated with oxymetazoline hydrochloride 0.05%+brimonidine tartrate 0.2%). No local or systemic side effects were noted, and in particular, there was no rebound erythema or edema noted.

These trials demonstrate that selective $\alpha_1$ adrenergic receptor agonists and selective $\alpha_2$ adrenergic receptor agonists, used separately or in combination, when topically applied prior to a procedure that can/will induce purpura, will reduce the size and appearance of the purpuric macules/patches and is an effective treatment to hasten their resolution.

Example 3

The use of a topically applied $\alpha_2$ adrenergic agonist for the treatment and prevention of solar purpura ("actinic purpura", "Bateman's purpura"): In order to evaluate the effect of topically applied $\alpha_1$ and $\alpha_2$ adrenergic agonists on the prevention and treatment of solar purpura, a 78 year old male volunteer with a diagnosis of solar purpura of the forearms treated with a topically applied $\alpha_2$ adrenergic agonist containing solution. The test area comprised the right extensor forearm from the wrist to the elbow. Photos were taken and baseline scores for the solar purpura on his right dorsal forearm from the wrist to the elbow were measured 6 times over a 91 day period before initiating treatment. Two measurements were taken to approximate the area of each purpuric patch. The measurements ranged from 0 cm$^2$ to 9.98 cm$^2$ and the mean over 6 measurements was 3.67 cm$^2$. (See Table 1)

A solution of brimonidine tartrate 0.2% (Bausch & Lomb Inc.) containing: brimonidine tartrate 0.02%, citric acid, polyvinyl alcohol, sodium chloride, sodium citrate, purified water, and benzalkonium chloride (0.005%) was applied by the patient to the right dorsal forearm twice daily (morning and evening). The solution was applied with a cotton ball to the skin of the entire right extensor forearm from the wrist to the elbow. The sites were followed clinically and photographically.

Seven days after starting, the patient returned for evaluation. The total area of purpura on the right dorsal forearm were measured and equaled 1.48 cm$^2$ (a decrease of 60% compared to mean baseline). The patient continued to apply brimonidine 0.2% solution to the right dorsal forearm twice daily (morning and evening).

Fourteen days after starting, the patient returned for evaluation. The total area of purpura on the right dorsal forearm were measured and equaled 0.35 cm$^2$ (a decrease of 90% compared to mean baseline). The patient continued to apply brimonidine 0.2% solution to the right dorsal forearm twice daily (morning and evening).

Twenty four days after starting, the patient returned for evaluation. The total area of purpura on the right dorsal forearm were measured and equaled 5.72 cm$^2$ (an increase of 34% compared to mean baseline). The patient reported that he had recently been gardening and had noted significant increase in the purpura after this activity despite continuing the topical medication. The patient continued to apply brimonidine 0.2% solution to the right dorsal forearm twice daily (morning and evening).

Thirty six days after starting, the patient returned for evaluation. The total area of purpura on the right dorsal forearm were measured and equaled 2.52 cm$^2$ (a decrease of 31% compared to mean baseline).

TABLE 1

| Day | Purpura Area(cm$^2$) | Effect | Notes |
| --- | --- | --- | --- |
| 0 | 3.67 | — | Baseline |
| 7 | 1.48 | ↓ 60% from Baseline | |
| 14 | 0.35 | ↓ 90% from Baseline | |
| 24 | 5.72 | ↑ 34% from Baseline | ↑ in purpura noted after gardening |
| 36 | 2.52 | ↓ 31% from Baseline | |

This trial demonstrates that the selective $\alpha_2$ adrenergic receptor agonist 0.2% brimonidine tartrate when topically applied twice daily to areas effected by solar ("actinic" or "senile" or "Bateman's") purpura reduces the size and appearance of purpuric macules/patches. Though significant intervening trauma to the region being treated (e.g. trauma to the arms from gardening) may still induce purpura, it is shown to be an effective treatment to hasten the resolution and decrease the appearance of purpura in actinically damaged or otherwise atrophic/damaged skin and cutaneous vessels.

Example 4

The use of a topically applied $\alpha_1$ adrenergic agonist for the treatment and prevention of solar purpura: In order to evaluate the effect of topically applied $\alpha_1$ adrenergic agonists on the prevention and treatment of solar purpura, two patient volunteers with the diagnosis of solar purpura of the forearms were treated with a topically applied selective $\alpha_1$ adrenergic agonist containing solution.

Subject 1 is a 78 year old man with a long-standing history of solar purpura on his forearms. The test area comprised the left dorsal (extensor) forearm from the wrist to the elbow. Pretreatment photos were taken and baseline measurements of the solar purpura on the left extensor forearm from the wrist to the elbow were measured. Two measurements were taken to approximate the area of each purpuric patch. The total area of purpura was 8.94 cm$^2$. (SEE TABLE 2)

A solution of oxymetazoline hydrochloride 0.05% (Afrin® Original 12 Hour Nasal Spray (Schering-Plough Healthcare Products) containing: oxymetazoline hydrochloride 0.05%, benzalkonium chloride solution, edetate disodium, polyethylene glycol, povidone, propylene glycol, purified water, sodium phosphate dibasic, sodium phosphate monobasic (0.005%)) was applied by the patient to the left dorsal forearm twice daily (morning and evening). The solution was applied with a cotton ball to the skin of the entire extensor forearm from the wrist to the elbow. The sites were followed clinically and photographically.

Seventeen days later, the patient returned for evaluation. The total area of purpura on the left extensor forearm were measured and equaled 9.95 cm$^2$ (an increase of 11% compared to baseline). The patient continued to apply oxymetazoline solution 0.05% to the left dorsal forearm twice daily (morning and evening).

Twenty nine days after starting, the patient returned for evaluation. The total area of purpura on the left extensor forearm were measured and equaled 5.73 cm$^2$ (a decrease of 36% compared to baseline). The patient continued to apply oxymetazoline solution 0.05% to the left dorsal forearm twice daily (morning and evening).

Forty four days after starting, the patient returned for evaluation. The total area of purpura on the left extensor forearm were measured and equaled 5.6 cm$^2$ (a decrease of 37% compared to baseline). The patient continued to apply oxymetazoline solution 0.05% to the left dorsal forearm twice daily (morning and evening).

Eighty one days after starting, the patient returned for evaluation. The total area of purpura on the left extensor forearm were measured and equaled 1.44 cm² (a decrease of 84% compared to baseline). The patient continued to apply oxymetazoline solution 0.05% to the left dorsal forearm twice daily (morning and evening).

Ninety one days after starting, the patient returned for evaluation. The total area of purpura on the left extensor forearm were measured and equaled 0.42 cm² (a decrease of 95% compared to baseline). The patient stopped applying the oxymetazoline containing solution on study day 91.

Seven days after stopping the oxymetazoline, the total area of purpura on the left extensor forearm was measured and equaled 1.96 cm². (an increase of 366% from the point of stopping medication (day 91 measurement)).

Fourteen days after stopping the oxymetazoline, the total area of purpura on the left extensor forearm was measured and equaled 0.46 cm². (an increase of 10% from the point of stopping medication (day 91 measurement)).

Twenty four days after stopping the oxymetazoline, the total area of purpura on the left extensor forearm was measured and equaled 2.22 cm². (an increase of 428% from the point of stopping medication (day 91 measurement)).

TABLE 2

| Day | Purpura Area(cm²) | Effect | Notes |
| --- | --- | --- | --- |
| 0 | 8.94 | — | Baseline |
| 17 | 9.95 | ↑ 11% from Baseline | |
| 29 | 5.73 | ↓ 36% from Baseline | |
| 44 | 5.6 | ↓ 37% from Baseline | |
| 81 | 1.44 | ↓ 84% from Baseline | |
| 91 | 0.42 | ↓ 95% from Baseline | Medication Discontinued Day 91 |
| 98 | 1.96 | ↑ 366% from Baseline | 7 Days off Medication |
| 112 | 0.46 | ↑ 10% from Baseline | 14 Days off Medication |
| 122 | 2.22 | ↑ 428% from Baseline | 24 Days off Medication |

The patient stated that he felt that there were fewer new purpuric macules/patches while he was using the medication, and he felt that when purpura occurred they seemed to resolve more quickly. The patient had no side effects, either local or systemic, during the treatment.

Subject 2 is an 87 year old woman with a long history of cosmetically disturbing solar purpura on her forearms who wanted to improve the appearance solar (decrease the purpura). The test area comprised the left dorsal (extensor) forearm from the wrist to the elbow. Pretreatment photos were taken and baseline measurements of the solar purpura on the left extensor forearm from the wrist to the elbow were measured. Two measurements were taken to approximate the area of each purpuric patch. The total area of purpura was 1.72 cm². (SEE TABLE 3)

A solution of oxymetazoline hydrochloride 0.05% (Afrin® Original 12 Hour Nasal Spray (Schering-Plough Healthcare Products) containing: oxymetazoline hydrochloride 0.05%, benzalkonium chloride solution, edetate disodium, polyethylene glycol, povidone, propylene glycol, purified water, sodium phosphate dibasic, sodium phosphate monobasic (0.005%)) was applied by the patient to the left dorsal forearm once daily (morning). The solution was applied with a cotton ball to the skin of the entire extensor forearm from the wrist to the elbow. The sites were followed clinically and photographically.

7 days later, the patient was reevaluated. The total area of purpura on the left dorsal forearm measured 0 cm² (a decrease of 100% compared to baseline). The patient continued to apply oxymetazoline solution 0.05% to the left extensor forearm once daily (morning).

31 days after starting, the patient was reevaluated. The total area of purpura on the left dorsal forearm measured 0 cm² (a decrease of 100% compared to baseline). The patient continued to apply oxymetazoline solution 0.05% to the left extensor forearm once daily (morning).

36 days after starting, the patient was reevaluated. The total area of purpura on the left extensor forearm measured 0.36 cm² (a decrease of 79% compared to baseline).

TABLE 3

| Day | Purpura Area(cm²) | Effect | Notes |
| --- | --- | --- | --- |
| 0 | 1.72 | — | Baseline |
| 7 | 0.00 | ↓ 100% from Baseline | |
| 31 | 0.00 | ↓ 100% from Baseline | |
| 36 | 0.36 | ↓ 79% from Baseline | |

The patient stated that she felt that there were fewer new purpuric patches while she was using the medication, and in her estimation the purpura that did occur seemed to resolve more quickly. The patient had no side effects, either local or systemic, during the treatment.

These trials demonstrate that the selective $\alpha_1$ adrenergic receptor agonist oxymetazoline hydrochloride when topically applied once or twice daily to areas effected by solar purpura dramatically reduces the size and appearance of purpuric macules/patches and may eliminate them. Though continuing trauma to the region being treated (e.g. trauma to the arms from gardening) may still induce purpura, this treatment is shown to be an effective treatment to hasten the resolution and decrease the appearance of purpura in actinically damaged or otherwise atrophic/damaged skin and cutaneous vessels.

The invention claimed is:

1. A method for treating non-thrombocytopenic purpura in a subject comprising administering a therapeutically effective amount of an $\alpha$ adrenergic receptor agonist selected from a selective $\alpha_1$ adrenergic receptor agonist, a selective $\alpha_2$ adrenergic receptor agonist and combinations thereof.

2. The method of claim 1, wherein the $\alpha$ adrenergic receptor agonist is topically applied to the skin of the subject.

3. The method of claim 1, wherein the $\alpha$ adrenergic receptor agonist is locally delivered to the subject.

4. The method of claim 1, wherein the selective $\alpha_1$ adrenergic receptor agonist is selected from oxymetazoline, naphazoline, tetrahydrozoline, phenylephrine, xylometazoline, methoxamine, metaraminol, midodrine, desglymidodrine, cirazoline, amidephrine and combinations thereof.

5. The method of claim 1, wherein the selective $\alpha_1$-adrenergic receptor agonist is selected from oxymetazoline, naphazoline, tetrahydrozoline, phenylephrine hydrochloride and combinations thereof.

6. The method of claim 1, wherein the selective $\alpha_2$ adrenergic receptor agonist is selected from brimonidine, clonidine, guanfacine, guanabenz, apraclonidine, xylazine, medetomidine, dexmedetomidine, $\alpha$-methyldopa, and combinations thereof.

7. The method of claim 1, wherein the selective $\alpha_2$-adrenergic receptor agonist is brimonidine.

8. The method of claim 1 further comprising administering a therapeutically effective amount of at least one other active agent selected from antibacterial agents, antiparasitic agents, antifungal agents, anti-inflammatory agents, antihistamines, anti-pruriginous agents, anesthetics, antiviral agents, keratolytic agents, anti free-radical agents, antioxidants, vitamin K, vitamin E, vitamin C, vitamin A, superoxide dismutase derivatives of plants, sesquiterpene lactones, antiseborrheic agents, antidandruff agents, antiacne agents, sunscreens and sun blocking agents, and active agents which modify at least one of cutaneous differentiation, proliferation, and pigmentation, including but not limited to tretinoin, retinol, retinal, alpha hydroxyl acids, beta hydroxyl acids and combinations thereof.

9. The method of claim 1, wherein said α adrenergic receptor agonist is administered in a pharmacologically acceptable form selected from solutions, gels, lotions creams, ointments, foams, emulsions, microemulsions, milks, serums, aerosols, sprays, dispersions, microcapsules, vesicles and microparticles thereof, soaps, and cleansing bars.

10. A method for decreasing non-thrombocytopenic purpura in a subject comprising administering a therapeutically effective amount of an α adrenergic receptor agonist selected from a selective $\alpha_1$ adrenergic receptor agonist, a selective $\alpha_2$ adrenergic receptor agonist and combinations thereof.

11. The method of claim 10, wherein the α adrenergic receptor agonist is topically applied to the skin of the subject.

12. The method of claim 10, wherein the α adrenergic receptor agonist is locally delivered to the subject.

13. The method of claim 10, wherein the selective $\alpha_1$ adrenergic receptor agonist is selected from oxymetazoline, naphazoline, tetrahydrozoline, phenylephrine, xylometazoline, methoxamine, metaraminol, midodrine, desglymidodrine, cirazoline, amidephrine and combinations thereof.

14. The method of claim 10, wherein the selective $\alpha_1$-adrenergic receptor agonist is selected from oxymetazoline, naphazoline, tetrahydrozoline, phenylephrine hydrochloride and combinations thereof.

15. The method of claim 10, wherein the selective $\alpha_2$ adrenergic receptor agonist is selected from brimonidine, clonidine, guanfacine, guanabenz, apraclonidine, xylazine, medetomidine, dexmedetomidine, α-methyldopa, and combinations thereof.

16. The method of claim 10, wherein the selective $\alpha_2$-adrenergic receptor agonist is brimonidine.

17. The method of claim 10 further comprising administering a therapeutically effective amount of at least one other active agent selected from antibacterial agents, antiparasitic agents, antifungal agents, anti-inflammatory agents, antihistamines, anti-pruriginous agents, anesthetics, antiviral agents, keratolytic agents, anti free-radical agents, antioxidants, vitamin K, vitamin E, vitamin C, vitamin A, superoxide dismutase derivatives of plants, sesquiterpene lactones, antiseborrheic agents, antidandruff agents, antiacne agents, sunscreens and sun blocking agents, and active agents which modify at least one of cutaneous differentiation, proliferation, and pigmentation, including but not limited to tretinoin, retinol, retinal, alpha hydroxyl acids, beta hydroxyl acids and combinations thereof.

18. The method of claim 10, wherein said α adrenergic receptor agonist is administered in a pharmacologically acceptable form selected from solutions, gels, lotions creams, ointments, foams, emulsions, microemulsions, milks, serums, aerosols, sprays, dispersions, microcapsules, vesicles and microparticles thereof, soaps, and cleansing bars.

19. A method for decreasing purpura in a subject from a surgical procedure comprising administering a therapeutically effective amount of an α adrenergic receptor agonist selected from a selective $\alpha_1$ adrenergic receptor agonist, a selective $\alpha_2$ adrenergic receptor agonist and combinations thereof to the site of said surgical procedure.

20. The method of claim 19, wherein the α adrenergic receptor agonist is topically applied to said site of said surgical procedure.

21. The method of claim 19, wherein the α adrenergic receptor agonist is locally delivered to the site of said surgical procedure.

22. The method of claim 19, wherein the selective $\alpha_1$ adrenergic receptor agonist is selected from oxymetazoline, naphazoline, tetrahydrozoline, phenylephrine, xylometazoline, methoxamine, metaraminol, midodrine, desglymidodrine, cirazoline, amidephrine and combinations thereof.

23. The method of claim 19, wherein the selective $\alpha_1$-adrenergic receptor agonist is selected from oxymetazoline, naphazoline, tetrahydrozoline, phenylephrine hydrochloride and combinations thereof.

24. The method of claim 19, wherein the selective $\alpha_2$ adrenergic receptor agonist is selected from brimonidine, clonidine, guanfacine, guanabenz, apraclonidine, xylazine, medetomidine, dexmedetomidine, α-methyldopa, and combinations thereof.

25. The method of claim 19, wherein the selective $\alpha_2$-adrenergic receptor agonist is brimonidine.

26. The method of claim 19 further comprising administering a therapeutically effective amount of at least one other active agent selected from antibacterial agents, antiparasitic agents, antifungal agents, anti-inflammatory agents, antihistamines, anti-pruriginous agents, anesthetics, antiviral agents, keratolytic agents, anti free-radical agents, antioxidants, vitamin K, vitamin E, vitamin C, vitamin A, superoxide dismutase derivatives of plants, sesquiterpene lactones, antiseborrheic agents, antidandruff agents, antiacne agents, sunscreens and sun blocking agents, and active agents which modify at least one of cutaneous differentiation, proliferation, and pigmentation, including but not limited to tretinoin, retinol, retinal, alpha hydroxyl acids, beta hydroxyl acids and combinations thereof.

27. The method of claim 19, wherein said α adrenergic receptor agonist is administered in a pharmacologically acceptable form selected from solutions, gels, lotions creams, ointments, foams, emulsions, microemulsions, milks, serums, aerosols, sprays, dispersions, microcapsules, vesicles and microparticles thereof, soaps, and cleansing bars.

28. The method of claim 19, wherein said surgical procedure is a laser treatment.

29. The method of claim 19, wherein said therapeutically effective amount of an α adrenergic receptor agonist is administered prior to said surgical procedure.

30. The method of claim 19, wherein said therapeutically effective amount of an α adrenergic receptor agonist is administered during said surgical procedure.

31. The method of claim 19, wherein said therapeutically effective amount of an α adrenergic receptor agonist is administered after said surgical procedure.

32. The method of claim 1, wherein non-thrombocytopenic purpura is selected from physical trauma induced purpura and solar purpura.

33. The method of claim 10, wherein non-thrombocytopenic purpura is selected from physical trauma induced purpura and solar purpura.

* * * * *

UNITED STATES PATENT AND TRADEMARK OFFICE
CERTIFICATE OF CORRECTION

PATENT NO. : 8,114,898 B2
APPLICATION NO. : 12/272253
DATED : February 14, 2012
INVENTOR(S) : Stuart D. Shanler et al.

Page 1 of 1

It is certified that error appears in the above-identified patent and that said Letters Patent is hereby corrected as shown below:

On the first page, in field (75), in "Inventors", in column 1, line 1, delete "Pamona," and insert -- Pomona, --, therefor.

On the first page, in field (56), under "Other Publications", in column 2, line 2-3, delete "Lippinocott Williams &Wilkins: Philiadelphia," and insert -- Lippincott Williams & Wilkins: Philadelphia, --, therefor.

On the first page, in field (56), under "Other Publications", in column 2, line 13, delete "Fluoruracil"" and insert -- Fluorouracil" --, therefor.

In column 3, line 15, after "techniques" insert -- . --.

In column 3, line 63, delete "trifluoromethan" and insert -- trifluoromethane --, therefor.

In column 8, line 23-24, delete "arachadonic" and insert -- arachidonic --, therefor.

In column 16, line 56, delete "intramedularry," and insert -- intramedullary, --, therefor.

In column 16, line 57-58, delete "intravesicularly," and insert -- intravascularly, --, therefor.

In column 17, line 5, delete "intravesicularly," and insert -- intravascularly, --, therefor.

In column 21, line 34, delete "(Original" and insert -- Original --, therefor.

In column 27, line 14, in claim 9, delete "lotions creams," and insert -- lotions, creams, --, therefor.

In column 27, line 59, in claim 18, delete "lotions creams," and insert -- lotions, creams, --, therefor.

In column 28, line 43, in claim 27, delete "lotions creams," and insert -- lotions, creams, --, therefor.

Signed and Sealed this
Tenth Day of April, 2012

David J. Kappos
*Director of the United States Patent and Trademark Office*